US006773560B2

(12) United States Patent
Pedersen et al.

(10) Patent No.: US 6,773,560 B2
(45) Date of Patent: **\*Aug. 10, 2004**

(54) DRY CONTACT ASSEMBLIES AND PLATING MACHINES WITH DRY CONTACT ASSEMBLIES FOR PLATING MICROELECTRONIC WORKPIECES

(75) Inventors: John M. Pedersen, Kalispell, MT (US); Jeremy Willey, Portland, OR (US); Daniel J. Woodruff, Kalispell, MT (US)

(73) Assignee: Semitool, Inc., Kalispell, MT (US)

( * ) Notice: Subject to any disclaimer, the term of this patent is extended or adjusted under 35 U.S.C. 154(b) by 122 days.

This patent is subject to a terminal disclaimer.

(21) Appl. No.: 09/823,948

(22) Filed: Mar. 30, 2001

(65) Prior Publication Data

US 2002/0000372 A1 Jan. 3, 2002

Related U.S. Application Data

(63) Continuation-in-part of application No. 09/717,927, filed as application No. PCT/US99/15847 on Jul. 9, 1999, now Pat. No. 6,527,925.
(60) Provisional application No. 60/119,668, filed on Feb. 11, 1999, and provisional application No. 60/112,232, filed on Dec. 7, 1998.

(51) Int. Cl.[7] .............................................. C25D 17/06
(52) U.S. Cl. ........................ 204/224 R; 204/197.01; 204/197.05; 204/197.14
(58) Field of Search .................. 204/297.01, 297.05, 204/297.06, 297.07, 297.1, 297.14, 224 R

(56) References Cited

U.S. PATENT DOCUMENTS

| 4,137,867 A | 2/1979 | Aigo |
| 4,246,088 A | 1/1981 | Murphy et al. |
| 4,259,166 A | 3/1981 | Whitehurst |

(List continued on next page.)

FOREIGN PATENT DOCUMENTS

| WO | WO 99/25904 | 5/1999 |
| WO | WO 99/25904 A | 5/1999 |
| WO | WO 99/25905 | 5/1999 |
| WO | WO 99/25905 A | 5/1999 |
| WO | WO 00/03072 | 1/2000 |
| WO | WO 00/03702 A | 1/2000 |
| WO | WO 00/32835 | 6/2000 |
| WO | WO 00/32835 A | 6/2000 |

OTHER PUBLICATIONS

U.S. patent application Ser. No. 09/386,558, Woodruff et al., filed Aug. 31, 1999.

(List continued on next page.)

Primary Examiner—Nam Nguyen
Assistant Examiner—Brian L Mutschler
(74) Attorney, Agent, or Firm—Perkins Coie LLP

(57) ABSTRACT

Contact assemblies, electroplating machines with contact assemblies, and methods for making contact assemblies that are used in the fabrication of microelectronic workpieces. The contact assemblies can be dry-contact assemblies. A contact assembly for use in an electroplating system can comprise a support member and a contact system carried by the support member. The support member, for example, can be a ring or another structure that has an opening configured to receive the workpiece. In one embodiment, the support member is a conductive ring. The contact system can have a plurality of contact members projecting inwardly into the opening relative to the support member. The contact members can comprise electrically conductive biasing elements that have contact sites and the contact members can also have a dielectric coating covering at least a portion of the biasing elements. The contact system can also have a shield carried by the support member and a seal on the lip of the shield. The shield and seal are configured to prevent electroplating solution from engaging the contact members.

70 Claims, 6 Drawing Sheets

U.S. PATENT DOCUMENTS

| | | |
|---|---|---|
| 4,304,641 A | 12/1981 | Grandia et al. |
| 4,341,629 A | 7/1982 | Uhlinger |
| 4,422,915 A | 12/1983 | Wielonski et al. |
| 4,466,864 A | 8/1984 | Bacon et al. |
| 4,576,685 A | 3/1986 | Goffredo et al. |
| 4,685,414 A | 8/1987 | DiRico |
| 4,913,085 A | 4/1990 | Vöhringer et al. |
| 5,135,636 A | 8/1992 | Yee et al. |
| 5,139,818 A | 8/1992 | Mance |
| 5,227,041 A | 7/1993 | Brogden et al. |
| 5,271,953 A | 12/1993 | Litteral |
| 5,310,580 A | 5/1994 | O'Sullivan et al. |
| 5,344,491 A | 9/1994 | Katou |
| 5,389,496 A | 2/1995 | Calvert et al. |
| 5,441,629 A | 8/1995 | Kosaki |
| 5,443,707 A | 8/1995 | Mori |
| 5,447,615 A | 9/1995 | Ishida |
| 5,500,315 A | 3/1996 | Calvert et al. |
| 5,522,975 A | 6/1996 | Andricacos et al. |
| 5,550,315 A | 8/1996 | Stormont |
| 5,597,460 A | 1/1997 | Reynolds |
| 5,597,836 A | 1/1997 | Hackler et al. |
| 5,609,239 A | 3/1997 | Schlecker |
| 5,670,034 A | 9/1997 | Lowery |
| 5,744,019 A | 4/1998 | Ang |
| 5,747,098 A | 5/1998 | Larson |
| 5,776,327 A | 7/1998 | Botts et al. |
| 5,788,829 A | 8/1998 | Joshi et al. |
| 5,843,296 A | 12/1998 | Greenspan |
| 5,904,827 A | 5/1999 | Reynolds |
| 5,932,077 A | 8/1999 | Reynolds |
| 5,957,836 A | 9/1999 | Johnson |
| 5,985,126 A | 11/1999 | Bleck et al. |
| 6,001,235 A | 12/1999 | Arken et al. |
| 6,080,291 A | 6/2000 | Woodruff et al. |
| 6,139,712 A | 10/2000 | Patton et al. |
| 6,156,167 A | 12/2000 | Patton et al. |
| 6,267,853 B1 | 7/2001 | Dordi et al. |
| 6,303,010 B1 | 10/2001 | Woodruff et al. |
| 6,309,520 B1 | 10/2001 | Woodruff et al. |
| 6,309,524 B1 | 10/2001 | Woodruff et al. |
| 6,540,899 B2 * | 4/2003 | Keigler .................. 205/118 |
| 6,579,430 B2 * | 6/2003 | Davis et al. ............ 204/297.01 |
| 2002/0053510 A1 * | 5/2002 | Woodruff et al. ....... 204/224 R |
| 2003/0010640 A1 * | 1/2003 | Kholodenko ............... 205/80 |

OTHER PUBLICATIONS

U.S. patent application Ser. No. 09/717,927, Batz, filed Nov. 20, 2000.

U.S. patent application Ser. No. 09/944,152, Woodruff et al., Aug. 30, 2001.

U.S. patent application Ser. No. 09/998,142, Woodruff et al., Oct. 31, 2001.

Semitool, Inc.; Quotation for Sale of Plating Tool; Single Substrate Processor Division; Quote 96–135e; Dated Jul. 24, 1996; pp. 1–5.

Semitool, Inc.; Design Review for Equinox Tool; Plater Quote 96–135e; Dated Jul. 15, 1996; pp. 1–20.

* cited by examiner

DRY CONTACT ASSEMBLIES AND PLATING MACHINES WITH DRY CONTACT ASSEMBLIES FOR PLATING MICROELECTRONIC WORKPIECES

RELATED APPLICATIONS

This application is a continuation-in-part of pending U.S. patent application Ser. No. 09/717,927, filed Nov. 20, 2000, and issued as U.S. Pat. No. 6,527,925; which is a continuation-in-part of International Application No. PCT/US99/15847, the specification of which was filed in English on Jul. 9, 1999; which claims priority from U.S. Provisional Application No. 60/119,668, filed Feb. 11, 1999, U.S. Provisional Application No. 60/112,232, filed Dec. 7, 1998, and U.S. patent application Ser. No. 09/113,723, filed Jul. 10, 1998, and issued as U.S. Pat. No. 6,080,291, all of which are incorporated herein by reference in their entirety.

BACKGROUND

Processors, memory devices, field-emission-displays, read/write heads and other microelectronic devices generally have integrated circuits with microelectronic components. A large number of individual microelectronic devices are generally formed on a semiconductor wafer, a glass substrate, or another type microelectronic workpiece. In a typical fabrication process, one or more layers of metal are formed on the workpieces at different stages of fabricating the microelectronic devices to provide material for constructing interconnects between various components.

The metal layers can be applied to the workpieces using several techniques, such as chemical vapor deposition (CVD), physical vapor deposition (PVD), plasma-enhanced deposition processes, electroplating, and electroless plating. The particular technique for applying a metal to a workpiece is a function of the particular type of metal, the structure that is being formed on the workpiece, and several other processing parameters. For example, CVD and PVD techniques are often used to deposit aluminum, nickel, tungsten, solder, platinum and other metals. Electroplating and electroless plating techniques can be used deposit copper, solder, permalloy, gold, silver, platinum and other metals. Electroplating and electroless plating can be used to form blanket layers and patterned layers. In recent years, processes for plating copper have become increasingly important in fabricating microelectronic devices because copper interconnects provide several advantages compared to aluminum and tungsten for high-performance microelectronic devices.

Electroplating is typically performed by forming a thin seed-layer of metal on a front surface of a microelectronic workpiece, and then using the seed-layer as a cathode to plate a metal layer onto the workpiece. The seed-layer can be formed using PVD, CVD or electroless plating processes. The seed-layer is generally formed on a topographical surface having vias, trenches, and/or other features, and the seed-layer is approximately 500–1000 angstroms thick. The metal layer is then plated onto the seed-layer using an electroplating technique to a thickness of approximately 6,000 to 15,000 angstroms. As the size of interconnects and other microelectronic components decrease, it is becoming increasingly important that the plated metal layer (a) has a uniform thickness across the workpiece, (b) completely fills the vias/trenches, and (c) has an adequate grain size.

Electroplating machines for use in manufacturing microelectronic devices often have a number of single-wafer electroplating chambers. A typical chamber includes a container for holding an electroplating solution, an anode in the container to contact the electroplating solution, and a support mechanism having a contact assembly with electrical contacts that engage the seed-layer. The electrical contacts are coupled to a power supply to apply a voltage to the seed-layer. In operation, the front surface of the workpiece is immersed in the electroplating solution so that the anode and the seed-layer establish an electrical field that causes metal in a diffusion layer at the front surface of the workpiece to plate onto the seed-layer.

The structure of the contact assembly can significantly influence the uniformity of the plated metal layer because the plating rate across the surface of the microelectronic workpiece is influenced by the distribution of the current (the "current density") across the seed-layer. One factor that affects the current density is the distribution of the electrical contacts around the perimeter of the workpiece. In general, a large number of discrete electrical contacts should contact the seed-layer proximate to the perimeter of the workpiece to provide a uniform distribution of current around the perimeter of the workpiece. Another factor that affects the current density is the formation of oxides on the seed-layer. Oxides are generally resistive, and thus oxides reduce the efficacy of the electrical connection between the contacts and the seed-layer. Still other factors that can influence the current density are (a) galvanic etching between the contacts and the seed-layer, (b) plating on the contacts during a plating cycle, (c) gas bubbles on the seed-layer, and (d) other aspects of electroplating that affect the quality of the connection between the contacts and the seed-layer or the fluid dynamics at the surface of the workpiece. The design of the contact assembly should address these factors to consistently provide a uniform current density across the workpiece.

One type of contact assembly is a "dry-contact" assembly having a plurality of electrical contacts that are sealed from the electroplating solution. For example, U.S. Pat. No. 5,227,041 issued to Brogden et al. discloses a dry contact electroplating structure having a base member for immersion into an electroplating solution, a seal ring positioned adjacent to an aperture in the base member, a plurality of contacts arranged in a circle around the seal ring, and a lid that attaches to the base member. The seal ring is placed in a channel of the base member. In operation, a workpiece is placed in the base member so that the front face of the workpiece engages the contacts and the seal ring. When the front face of the workpiece is immersed in the electroplating solution, the seal ring prevents the electroplating solution from engaging the contacts inside the base member.

U.S. Pat. No. 6,156,167 issued to Patton et al. (Patton) discloses another apparatus for electroplating the wafer surface. The devices disclosed in Patton include a cup having a center aperture defined by an inner perimeter, a compliant seal adjacent to the inner perimeter, contacts adjacent to the compliant seal, and a cone attached to a rotatable spindle. The cup can be formed of an electrically insulating material, such as polyvinylidene fluoride (PVDF) or chlorinated polyvinyl chloride (CPVC). Alternatively, the cup can be formed of an electrically conductive material, such as aluminum or stainless steel. The compliant seal engages a perimeter region of the wafer surface to prevent the plating solution from contaminating the wafer edge, the backside of the wafer, and the contacts. The compliant seal is formed of a relatively soft material, such as VITON (manufactured by DuPont®) or CHEMRAZ (manufactured by Green Tweed). In operation, a surface of the cone presses against the backside of the wafer to force a perimeter region of the wafer against the compliant seal.

The devices disclosed in Brogden and Patton may entrap bubbles on the plating surface of a wafer at the inner perimeter of the compliant seal. One feature of these devices that inhibits bubbles from flowing off of the plating surface is the "well-depth," which is defined by the thickness of the seal and the base member that holds the seal. In Brogden, for example, the combined thickness of the seal and the base member appears to be quite large such that it is expected that bubbles will accumulate at the interior perimeter of the seal during operation. It appears that Patton is an improvement over Brogden, but Patton also appears to have a significant well-depth at the inner perimeter of its compliant seal. The depth of the inner perimeter of the cup and the compliant seal in Patton, for example, is disclosed as being approximately 0.147 inch. Therefore, the electroplating apparatus disclosed in Patton are also expected to allow bubbles to accumulate at the inner perimeter of the seal.

SUMMARY

The present invention is generally directed toward contact assemblies, electroplating machines with contact assemblies, and methods for making contact assemblies that are used in the fabrication of microelectronic workpieces. The contact assemblies are generally dry-contact assemblies that inhibit the electroplating solution from engaging the contacts or the backside of the workpieces. In one aspect of an embodiment, a contact assembly for use in an electroplating system comprises a support member and a contact system carried by the support member. The support member, for example, can be a ring or another structure having an opening configured to receive the workpiece. In one embodiment, the support member is a conductive ring, and the contact system can be coupled to the support member. The contact system can have a plurality of contact members projecting into the opening relative to the support member. The contact members can comprise electrically conductive biasing elements, such as fingers, that have a contact site or a contact tip. The contact members can project inwardly relative to the support member along a radius of the opening, or they can be "swept" at an angle to a radius of the opening. The contact members can also be cantilevered spring elements that support the workpiece, and they can have a raised feature configured to engage the seed-layer on the workpiece.

The contact assembly can also include a barrier or shield carried by the support member and an elastomeric seal carried by the shield. In one embodiment, the shield projects from the support member to extend under the contact members and into the opening, and the shield includes a lip region in the opening inward of the contact members. The shield can be a flexible member that has an inner edge inward of the contact sites and a "boundary line" between the inner edge and the contact sites. The seal can be an elastomeric seal that is molded or otherwise adhered to the lip region of the shield. In one embodiment, the seal can have a first edge at the inner edge of the shield and a second edge at the boundary line of the shield. The second edge of the seal defines its outer perimeter such that the seal does not extend underneath the contact members in selected embodiments.

In operation, a workpiece is loaded into the contact assembly by inserting the workpiece through the opening of the support member until the plating surface of the workpiece engages the contact sites on the contact members. Because the contact members can be biasing elements that flex, the contact members flex in the direction that the workpiece is moving and slide across the plating surface. This movement of the contacts enhances the interface between the contact sites and the seed-layer on the workpiece even though the plating surface of the workpiece may have vias, trenches and other topographical features. The plating surface also engages the seal, which prevents the electroplating solution from engaging the contact members. The face of the workpiece can then be immersed in an electroplating solution while the contact assembly rotates.

Several embodiments of contact assemblies with elastomeric seals are expected to provide a sufficient seal against the plating surface of the workpiece without entrapping bubbles at the perimeter of the workpiece or sticking to the workpiece after the plating cycle. For example, because the seals in several embodiments do not extend underneath the contact members, they can be thin to reduce the well depth. The well depth in selected embodiments can be less than 0.085 inch. Additionally, the width of the seals is limited to a seal zone between the contact sites and the inner edge of the shield to reduce the surface area of the seal that contacts the perimeter of the wafer. This inhibits the workpiece from sticking to the contact assembly after the plating cycle and allows more area on the plating surface to be available for components.

BRIEF DESCRIPTION THE DRAWINGS

DETAILED DESCRIPTION OF SELECTED EMBODIMENTS

The following description discloses the details and features of several embodiments of contact assemblies, methods for making contact assemblies, and electroplating machines with contact assemblies for electroplating materials onto microelectronic workpieces. It will be appreciated that several of the details set forth below are provided to describe the foregoing embodiments in a manner sufficient to enable a person skilled in the art to make and use contact assemblies and electroplating systems. Several of the details and advantages described below, however, may not be necessary to practice certain embodiments of the invention. Additionally, the invention can also include additional embodiments that are within the scope of the claims but are not described in detail with respect to FIGS. 1–9.

The operation and features of the contact assemblies are best understood in light of the environment and equipment in which they can be used to electroplate workpieces. As such, several embodiments of electroplating tools and reaction chambers that can be used with the contact assemblies will be described with reference to FIGS. 1 and 2. The details and features of several embodiments of contact assemblies will then be described with reference to FIGS. 3–9.

Figure 1:
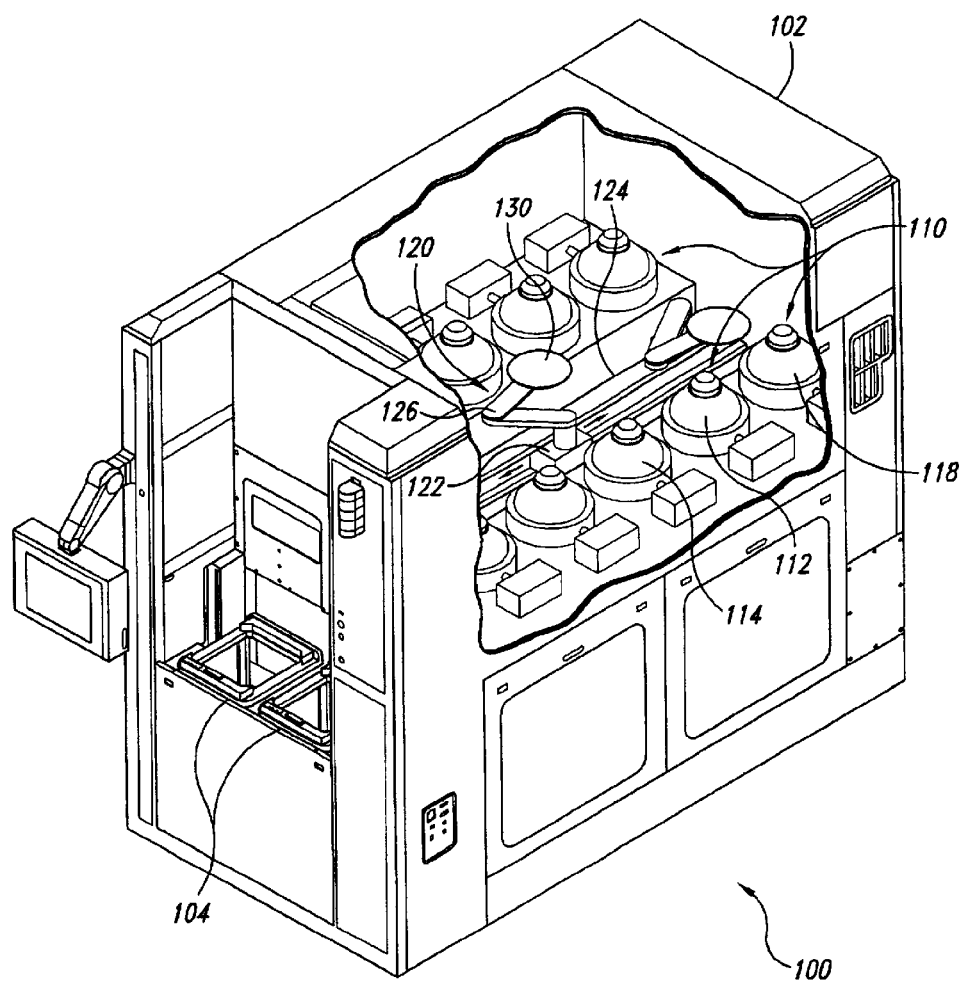
FIG. 1 is an isometric view with a cut-away portion of an electroplating machine having a contact assembly in accordance with one embodiment of the invention.

A. Selected Embodiments of Electroplating Machines and Reactor Chambers for use with Contact Assemblies to Electroplate Materials onto Microelectronic Workpieces FIG. 1 is a front isometric view of an electroplating machine 100 in which contact assemblies in accordance with embodiments of the invention can be used. The electroplating machine 100 can include a cabinet 102, a load/unload mechanism 104 at one end of the cabinet 102, and a plurality of chambers 110 in the cabinet 102. The chambers 110 can include electroplating chambers 112, electroless plating chambers 114, rapid thermal annealing chambers 118, and/or cleaning chambers. The electroplating machine 100 can also include a transfer mechanism 120 having a rail or track 122 and a plurality of robots 124 that move along the track 122. The robots 124 include arms 126 that can carry a microelectronic workpiece 130 between the chambers 110. In operation, the load/unload mechanism 104 positions a cassette or pod holding a plurality of workpieces either in the cabinet 102 or at an opening of the cabinet, and the transfer mechanism 120 handles the individual workpieces 130 inside the cabinet 102. The transfer mechanism 120, for example, can initially place the workpiece 130 in an electroless plating chamber 114 to repair or enhance the seed-layer on the workpiece. The transfer mechanism 120 can then remove the workpiece 130 from the electroless plating chamber 114 and place it in the electroplating chamber 112 for forming a blanket layer or a patterned layer on the front face of the workpiece 130. After the electroplating cycle, the transfer mechanism 120 can remove the workpiece 130 from the electroplating chamber 112 and transfer it to another processing station in the machine 100 (e.g., a standard rinser-dryer, a rinse/etch capsule, etc.) or place it in the cassette. In an alternative embodiment, the transfer mechanism can be a radial system such as in the EQUINOX® machines manufactured by Semitool, Inc. of Kalispell, Mont.

Figure 2:
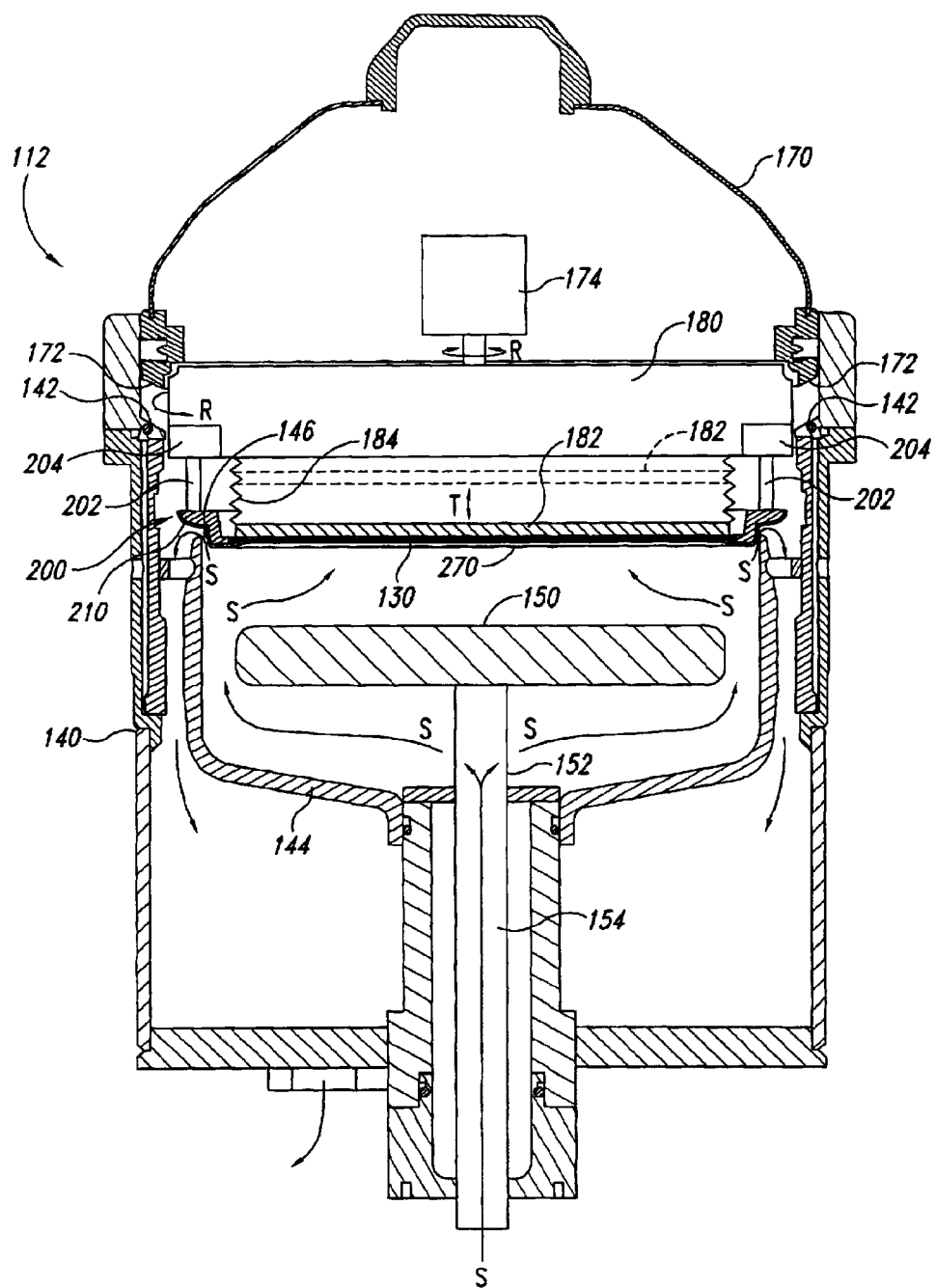
FIG. 2 is a cross-sectional view of an electroplating chamber having a contact assembly for use in an electroplating machine in accordance with an embodiment of the invention.

FIG. 2 is a partial cross-sectional view of an electroplating chamber 112 having a contact assembly 200 in accordance with one embodiment of the invention for supporting and providing an electrical connection to a front face or plating surface of the workpiece 130. For the purposes of brevity, several components of the electroplating chamber 112 are shown schematically or by line drawings. Many of the particular features of the components shown schematically are described more detail in the patent applications incorporated by reference. The electroplating chamber 112 can include a bowl 140 configured to contain an electroplating solution, an anode 150 in the bowl 140, and a head assembly 170 that carries the contact assembly 200. The head assembly 170 is movable with respect to the bowl 140 to position the workpiece 130 in the plating solution (not shown). When the head assembly 170 is fully inserted into the bowl 140, a beveled surface 172 of the head assembly 170 is superimposed over a corresponding beveled surface 142 of the bowl 140, and the contact assembly 200 holds the workpiece 130 in a desired position relative to the plating solution.

The bowl 140 can include a cup 144 having an overflow weir 146. The anode 150 is positioned in the cup 144, and the anode 150 can be carried by an anode support assembly 152. In one embodiment, the anode support assembly 152 has a channel 154 through which the electroplating solution flows and is discharged into the cup 144, but in other embodiments the electroplating solution can flow into the cup 144 separately from the anode support assembly 152. The anode support assembly 152 can be electrically conductive, or it can include a conductor to electrically couple the anode 150 to a power supply. In operation, a flow of plating solution (identified schematically by arrows "S") flows past the anode 150, over the weir 146, and into a lower portion of the bowl 140. As the flow of plating solution passes over the weir 146, it forms a meniscus at the top of the cup 144. The plating solution flow S can then pass out of the bowl 140 where it is filtered and reconditioned so that the plating solution can be re-circulated through the cup 144. Suitable embodiments of bowls 140, cups 144, anodes 150 and anode support assemblies 152 are described in PCT Application Nos. PCT/US99/15430, PCT/US00/10120, and PCT/US00/10210, all of which are herein incorporated in their entirety by reference.

The head assembly 170 can further include a motor 174 and a rotor 180 that carries the contact assembly 200. The motor 174 is coupled to the rotor 180 to rotate the contact assembly 200 and the workpiece 130 during a plating cycle (Arrow R). The rotor 180 can include a movable backing plate 182 and a seal 184. The backing plate 182 can move transverse to the workpiece 130 (Arrow T) between a first position in which the backing plate 182 engages the back side of the workpiece 130 (shown in solid lines in FIG. 2) and a second position in which it is spaced apart from the back side of the workpiece 130 (shown in broken lines in FIG. 2). In this embodiment, the contact assembly 200 is coupled to the rotor 180 by a plurality of shafts 202 that are received in quick-release mechanisms 204. The shafts 202 can be rigid, conductive members that electrically couple the contact assembly 200 to an electrical potential so that the seed-layer on the workpiece 130 is a cathode for plating or an anode for electropolishing.

In operation, the head assembly 170 can be initially raised above the bowl 140 and rotated about a relatively horizontal axis so that the plating surface of the contact assembly 200 faces upward away from the bowl 140. The backing plate 182 is moved to the second position in which it is spaced apart from the contact assembly 200 to load the workpiece 130 into the head assembly 170. The robot 124 (FIG. 1) inserts the workpiece 130 face-up into the contact assembly 200, and then the backing plate 182 moves to the first position in which it presses the workpiece 130 against the contact assembly 200. The head assembly 170 then rotates about the horizontal axis to position the contact assembly 200 face downward and lowers the loaded workpiece 130 and a portion of the contact assembly 200 into the plating solution proximate to the overflow weir 146. The motor 174 rotates the rotor 180 to move the workpiece 130 in the plating solution during the plating cycle. After the plating cycle is complete, the head assembly 170 removes the workpiece 130 from the plating solution so that it can be rinsed and/or transferred to another processing chamber or machine. In an alternative embodiment, the head assembly does not rotate about the horizontal axis to position the contact assembly 200 face-up during a load/unload sequence such that the workpiece is loaded into the contact assembly face-down toward the bowl 140.

The foregoing description of the electroplating machine 100 and the electroplating chamber 112 provides examples of the types of devices in which contact assemblies in accordance with embodiments of the invention can be used to plate metal layers onto microelectronic workpieces. It will be appreciated that the contact assembly 200, and other embodiments of contact assemblies described in more detail below, can be used with other electroplating machines and reaction chambers.

B. Selected Embodiments of Contact Assemblies for Electroplating Microelectronic Workpieces FIGS. 3–9 illustrate several embodiments of contact assemblies that can be used in the electroplating chamber 112 of the electroplating machine 100. The structures and operation of the contact assemblies shown in FIGS. 3–9 are generally described with reference to electroplating applications. It will be appreciated, however, that they can also be configured to be non-electrical workpiece support assemblies for use in electroless plating applications.

Figure 3:
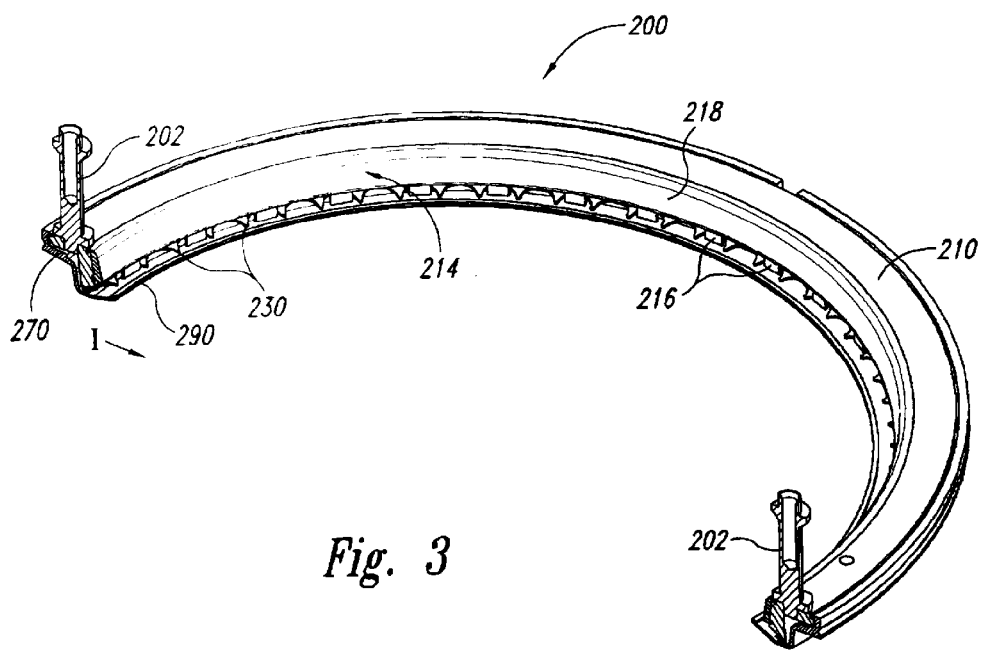
FIG. 3 is an isometric view illustrating a portion of a contact assembly for use in an electroplating machine in accordance with an embodiment of the invention.

FIG. 3 is an isometric view showing the features of an embodiment of the contact assembly 200 in greater detail. In this embodiment, the contact assembly 200 has a support member 210, a contact system 230 carried by the support member 210, and a barrier or shield 270 carried by the support member 210. The contact assembly 200 can also have a seal 290 carried by the shield 270. In one embodiment, a plurality of shafts 202 can be connected to the support member 210 to attach the contact assembly 200 to the head assembly 170 (FIG. 2).

The embodiment of the support member 210 shown in FIG. 3 is a ring defining an opening that is configured to receive the workpiece 130 (FIG. 2). The support member 210 can have a circular shape, a shape with one or more straight-edge sections, or any other suitable shape corresponding to the shape of the workpiece. More specifically, the workpiece 130 can move through the support member 210 along a load/unload path "P." The support member 210 can be formed of a conductive material, such as titanium, stainless-steel, or another suitable metal. In an alternative embodiment, the support member 210 can be formed of a dielectric material and further include electrically conductive lines extending through or along the dielectric material. In this embodiment, the support member 210 includes a guide ring 214 with tabs 216 that project downwardly between contact members of the contact system 230. The guide ring 214 can also have an inclined surface 218 that slopes radially inwardly toward the contact system 230 to guide the workpiece onto the contact system. The guide ring 214 is typically formed of a dielectric material.

Figure 4:
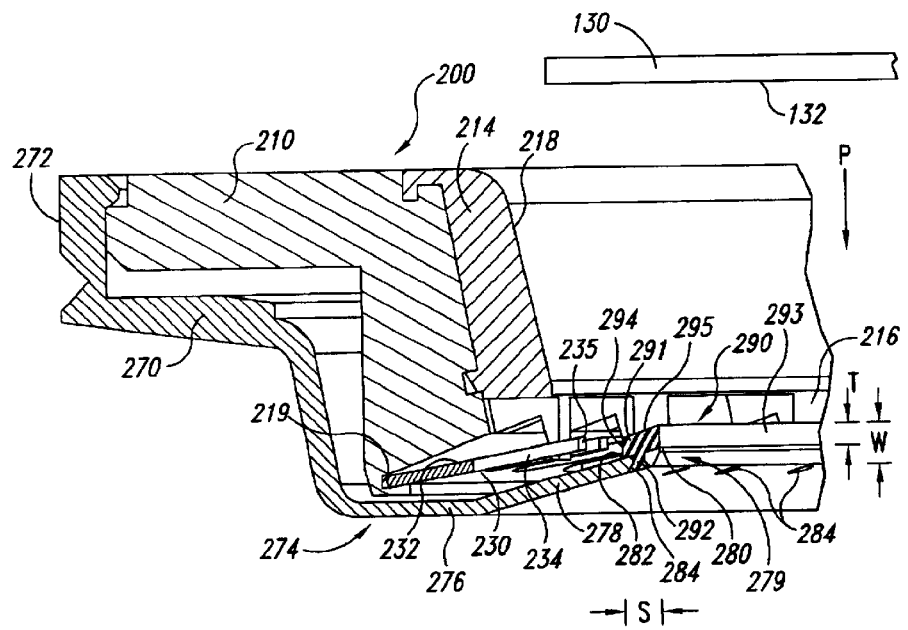
FIG. 4 is an isometric view illustrating a cross-section of a contact assembly for use in an electroplating machine in accordance with an embodiment of the invention.

FIG. 4 is an isometric view illustrating a cross-sectional portion of the contact assembly 200 in greater detail. The contact system 230 can comprise a conductive mounting section 232 and a plurality of contact members 234 projecting from the mounting section 232. The mounting section 232, for example, can be a ring or another type of base that is positioned in an annular slot 219 of the support member 210. In one embodiment, the mounting section 232 is a conical ring. The mounting section 232 can also be attached to the support member 210 by spot welds, screws, or other suitable techniques. The mounting section 232 can alternatively be a segment, such as an arcuate segment or an annular segment of a ring, and a plurality of separate segments can be attached to the support member 210. The mounting section 232 and the contact members 234 can be formed of an electrically conductive material and/or have a suitable electrically conductive coating. In one embodiment, the mounting section 232 and the contact members 234 are made from a sheet of metal, such as titanium, stainless-steel, or another suitably conductive material that can flex under the loads generated by the backing plate 182 as it presses the workpiece 130 against the contact members 234.

The contact members 234 can be conductive biasing elements that project inwardly into the opening defined by the support member 210 and transversely with respect to the load/unload path P. In one embodiment, the contact members 234 are cantilevered spring elements. The contact members 234 can be integral with the mounting section 232, or they can be individual fingers that are attached to the mounting section 232 by spot welds or other suitable fasteners. In this embodiment, the contact members 234 are cantilevered spring elements or fingers that project inwardly along a radius of the support member 210 and upwardly toward the guide ring 214.

The shield 270 is carried by the support member 210 to prevent the electroplating solution from engaging the contact members 234. The shield 270 can include a first section 272 attached to the support member 210 and a second section 274 extending from the first section 272. The second section 274, for example, can extend from the first section 272 to project inwardly into the opening defined by the support member 210 (shown by arrow "I" in FIG. 3). In one embodiment, the second section 274 of the shield 270 has a first segment 276 and a second segment 278. The first segment 276 of the shield 270 can be positioned under the support member 210 and the mounting section 232 of the contact system 230. The second segment 278 of the shield 270 can project inwardly and upwardly from the first segment 276.

The shield 270 can also include a lip region 279 at the distal portion of the second segment 278. The lip region 279 can be defined by an inner most edge 280 of the shield 270 and a "boundary line" 282 radially outwardly of the inner edge 280. The boundary line 282 is generally between the inner edge 280 of the shield 270 and the contact sites 235 of the contact members 234. The inner edge 280 and the boundary line 282 define a seal zone S for contacting the workpiece (not shown).

The shield 270 can also include a plurality of apertures 284 in the seal zone S. In one embodiment, each aperture can have a beveled lower section with inclined side walls and an upper section extending above the lower section. The apertures 284 can also be cylindrical holes or the other configurations. For example, the shield 270 could have a plurality of slots in the seal zone S.

The contact assembly 200 further includes a seal 290 having an upper section 291 projecting above the shield 270 and a lower portion 292 in the apertures 284. The upper section 291 has a first edge 293 at least proximate to the inner edge 280 and a second edge 294 at least proximate to the boundary line 282. The second edge 294 accordingly defines the outer perimeter of the seal 290 in this embodiment. The seal 290 can also include a bearing surface 295 for contacting a plating surface 132 of the workpiece 130. The upper section 291 of the seal 290 can have a width defined by the distance between the first edge 293 and the second edge 294. The width of the seal 290 can be approximately 0.02–0.06 inch, and in many applications the width is approximately 0.03–0.05 inch. The upper section 291 of the seal 290 can also have a thickness T of approximately 0.02–0.04 inch, and in many applications the thickness T can be approximately 0.025–0.035 inch. In one embodiment, the well-depth W, which is defined by the thickness of the upper section 291 of the seal 290 and the thickness of the lip region 279 of the shield 270, is not greater than 0.14 inch, and more specifically not greater than approximately 0.06–0.10 inch.

The shield 270 can be formed of a dielectric material or a conductive material that is at least partially coated with a dielectric material. In one embodiment, the shield 270 is formed of polyetheretherketone (PEEK) or polyvinylidene fluoride (PVDF). The shield 270 can alternatively be composed of titanium with a platinum coating, titanium with a dielectric coating, or another suitable metal and/or coating that can be used in plating solutions. The seal 290 can be composed of an elastomeric material, such as a fluoroelastomer, a perfluoroelastomer, or another suitable material that is sufficiently compressible to conform to the topography of the plating surface 132 of a workpiece 130. Suitable fluoroelastomers include VITON® and AFLAS (manufactured by DuPont), and a suitable perfluoroelastomer is CHEMRAZ (also manufactured by DuPont).

The seal 290 is attached to the shield 270 by molding the seal onto the lip of the second segment 278 of the shield 270. In one embodiment, an elastomeric insert of the seal material is placed into a mold, and then the mold is clamped to the lip region 279 of the shield 270. The mold can then be heated and pressurized to shape the elastomeric insert within the mold into a desired shape for the upper section 291 of the seal 290 and to drive the lower section 292 of the seal 290 into the apertures 284. In an alternative embodiment, an adhesive such as CHEMLOK 5150 (manufactured by Lord Corporation of Pennsylvania) can be applied to the upper surface of the lip region 279 before the mold is clamped to the shield 270.

The contact assembly 200 provides electrical contact to a seed layer on a workpiece and prevents a plating solution from engaging the support member 210 and the contact system 230. In a typical application, the workpiece 130 is loaded into the contact assembly 200 by inverting the workpiece 130 and the contact assembly 200 so that the plating surface 132 of the workpiece 130 faces upward and the contact assembly 200 faces downward. The workpiece 130 is then moved along the load/unload path P so that the perimeter of the plating surface 132 initially contacts the bearing surface 295 of the seal 290. As the workpiece 130 continues to move along the load/unload path P, the shield 270 flexes away from the support member 210 until the plating surface 132 of the workpiece 130 engages the contact sites 235 of the contact members 234. In many applications, the workpiece 130 can continue to move along the load/unload path P for a limited distance, which causes the contact members 234 to flex away from the support member 210 and to slide inwardly along the plating surface 132 for a short distance. The workpiece 130 and the contact assembly 200 are then rotated so that the contact assembly 200 faces upward (as shown in FIG. 4), and the contact assembly 200 is lowered until the plating surface 132 engages a plating solution.

The contact assembly 200 is expected to provide an adequate seal against the plating surface 132 to prevent the plating solution from engaging the contact members 234 without trapping bubbles at the perimeter of the plating surface. One feature of several embodiments of the contact assembly 200 is that the thickness T of the upper section 291 of the seal 290 is sufficiently small so that bubbles flow over the first edge 293 of the seal 290. Additionally, the overall well depth W of the shield 270 and the seal 290 together is also sufficiently small to allow bubbles to move radially outwardly as the contact assembly 200 rotates during a plating cycle. The lip region 279 of the shield 270 can also be angled or rounded at the inner edge 280 to further enhance the flow of plating solution and bubbles radially outwardly under the exterior surface of the shield 270.

Therefore, several embodiments of the contact assembly 200 are expected to prevent the plating solution from engaging the contact members 234 in a manner that inhibits bubbles from residing at the perimeter of the plating surface during a plating cycle.

The contact assembly 200 is also expected to provide an adequate seal against the plating surface 132 without sticking to the plating surface. In many applications that use a viscous plating solution, the workpiece 130 may stick to the bearing surface 295 of the seal 290. This can be problematic because the workpiece 130 may not disengage the contact assembly 200 for unloading. This is also a problem because it may contaminate or otherwise foul the perimeter portion of the plating surface 132. One feature of several embodiments of the seal 290 is that it is relatively narrow to reduce the surface area that contacts the plating surface 132. Several embodiments of the contact assembly 200, for example, seek to strike a balance between providing a large surface area to create an adequate seal without covering too much of the surface area of the plating surface 132. The narrow width of the seal 290 is also valuable because it allows more surface area of the plating surface 132 to be used for producing components.

Figure 5:
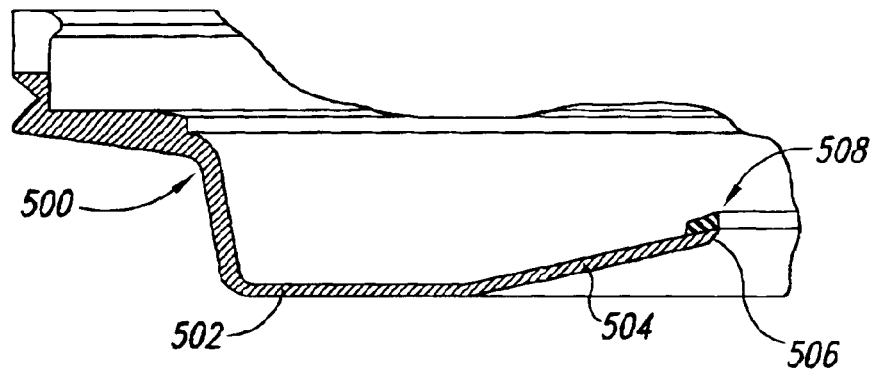
FIG. 5 is an isometric view illustrating a cross-section of a shield with a seal for use in a contact assembly in accordance with another embodiment of the invention.

FIG. 5 is an isometric view showing a cross-sectional portion of a shield 500 with a seal 508 for use in a contact assembly in accordance with another embodiment of the invention. The shield 500 can have a first segment 502 and a second segment 504 projecting inwardly from the first segment 502. The shield 500 can also have a lip region 506 at the inner portion of the second segment 504. The first and second segments 502 and 504 of the shield 500 can be substantially similar to the first and second segments 276 and 278 of the shield 270 shown in FIG. 4, except that the second segment 504 of the shield 500 does not include a plurality of apertures adjacent to the lip region 506. The seal 508 can be molded onto the top surface of the lip region 506. Additionally, the seal 508 can be adhered to the shield 500 by coating the upper surface of the lip 506 with an adhesive before molding the seal 508 on the shield 500. The shield 500 and the seal 508 can be composed of the same materials described above with reference to FIG. 4.

Figure 6:
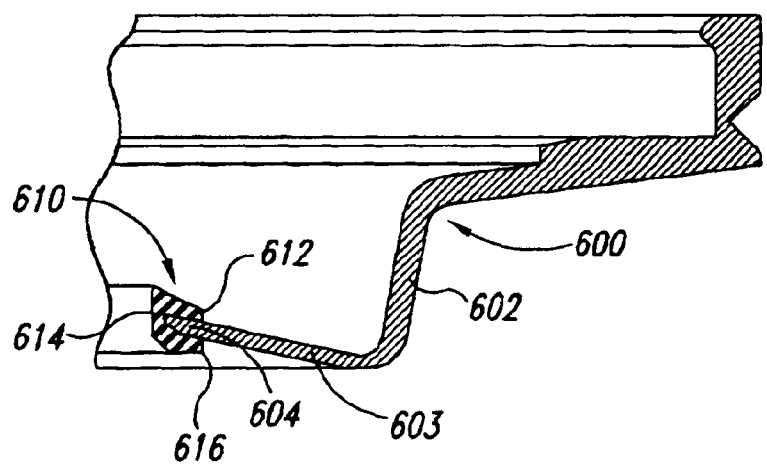
FIG. 6 is an isometric view illustrating a cross-section of a shield with a seal for use in a contact assembly in accordance with another embodiment of the invention.

FIG. 6 is an isometric view showing a cross-sectional portion of a shield 600 having a seal 610 for use in a contact assembly in accordance with another embodiment of the invention. The shield 600 can include a first section 602 configured to be attached to the support member (not shown in FIG. 6) and a second section 603 configured to extend inwardly from the first section 602. The second section 603 of the shield 600 can terminate at a lip region 604. The seal 610 can include an upper section 612 on the upper surface of the lip region 604, an intermediate section 614 that wraps around the distal portion of the lip region 604, and a lower section 616 on the lower surface of the lip region 604. The seal 610 can be formed by molding an elastomeric material onto the lip region 604 of the shield 600 in the shape of the seal 610. Additionally, an adhesive can be applied to the upper and lower surfaces of the lip region 604 before the seal 610 is molded onto the shield 600.

The seals 508 and 610 are expected to provide many of the same results and operate in substantially the same manner as the seal 290 shown in FIG. 4. The seal 508 can have a narrower width than the seal 290 shown in FIG. 4 because the shield 500 does not have a plurality of apertures at the lip region 506. Conversely, the lower section 292 in the apertures 284 of the shield 270 may provide a better bond between the seal 290 and the shield 270 than the seal 508 has with the shield 500. The seal 610 shown in FIG. 6 can provide a strong bond between the seal 610 and the shield 600, but the well depth of this system may not be suitable for some applications because the lower section 616 of the shield 610 may inhibit bubbles from flowing off of the plating surface of the workpiece during a plating cycle.

Figure 7:
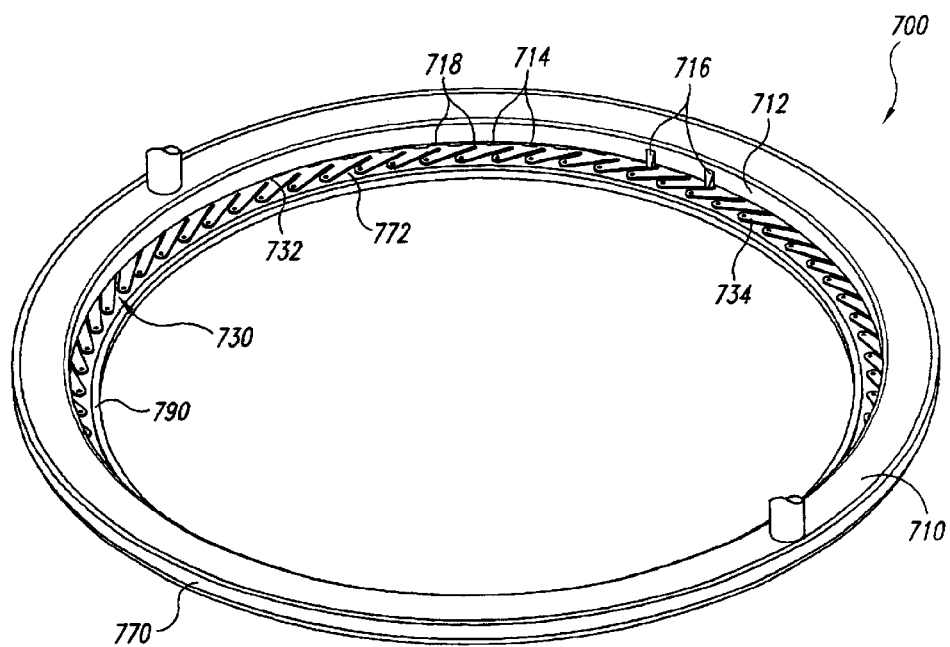
FIG. 7 is an isometric view of a contact assembly for use in an electroplating machine in accordance with another embodiment of the invention.

FIG. 7 is an isometric view of a contact assembly 700 in accordance with another embodiment of the invention for use in a reactor chamber of a plating machine. The contact assembly 700 can have a support member 710 and a contact system 730 comprising a plurality of swept or angled contact members 734. The contact assembly 700 can also have a shield 770 carried by the support member 710 and a seal 790 on the shield 770. The support member 710 can have an inner wall 712 or guide ring defining an opening for receiving the workpiece, a plurality of posts 714 spaced apart from one another by gaps 718, and a plurality of guides 716 arranged around the inner wall 712. The posts 714 of the support member 710 can have an angled lower surface that projects upward.

Figure 8:
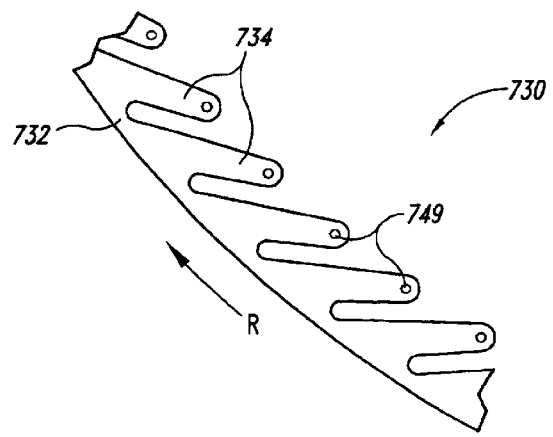
FIG. 8 is a top plan view of a contact system for use in the contact assembly of FIG. 7.

FIG. 8 is a top plan view illustrating a portion of an embodiment of the contact system 730 in greater detail. Referring to FIGS. 7 and 8 together, the contact system 730 can further comprise a mounting section 732, such as an annular ring, an annular segment, an arcuate segment, or another structure for mounting the contact members 734 to the support structure 710. The contact members 734 can project from the mounting section 732 inwardly into the opening of the support member 710 at an angle relative to a radius of the support member 710. Additionally, the contact members 734 can project upwardly in a manner similar to the contact members 234 shown in FIG. 4. In an alternative embodiment, the contact members 734 can extend along a radius of the support member 710 and/or extend generally horizontally. As explained in more detail below, several embodiments of the contact members 734 have a contact site 749 for engaging the seed layer on the workpiece.

Figure 9:
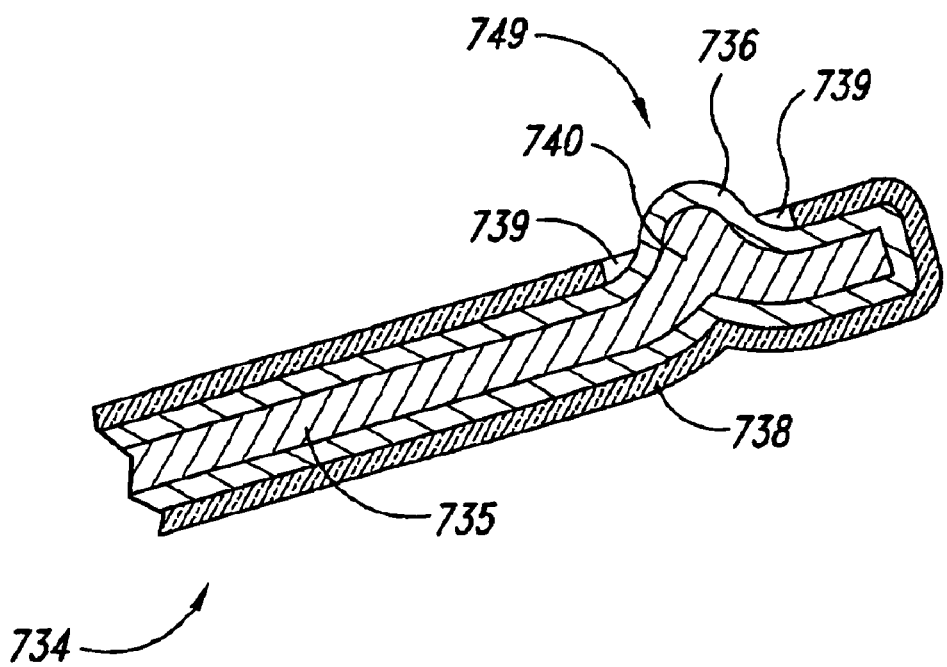
FIG. 9 is a cross-sectional view of a portion of a contact member in accordance with an embodiment of the invention.

The contact members 734 and the mounting section 732 can be coated with a dielectric material to further protect the contacts from the plating solution. FIG. 9 is a cross-sectional view of a contact member 734 comprising a biasing element 735 having a raised feature 740 at a contact site 749 for contacting the seed-layer of the workpiece. The biasing element 735 can be a finger made from titanium or another suitable conductive material with desirable structural qualities. A conductive contact layer 736 can coat the biasing element 735, and a dielectric coating 738 can cover the contact layer 736. The contact layer 736 can be platinum or another suitable metal, and the dielectric coating 738 can be any suitable dielectric film. The dielectric coating 738 is generally selected according to (a) the compatibility with the plating solution, (b) adhesion to the metal of the contact system 730, and (c) ability to effectively coat the contact system 730. Suitable materials that can be used for the dielectric coating 738 include (a) an 8840 primer and a Teflon dielectric exterior coating manufactured by DuPont® ("DuPont"); (b) an 8840 green coating manufactured by DuPont; (c) a 954-100 epoxy based coating manufactured by DuPont; (d) a 954-101 epoxy based coating manufactured by DuPont; (e) HALAR® coatings under the name Dycore®404; (f) KYNAR® coatings under the identification Dycore® 202 either with or without a primer of Dycore 204; (g) HALAR® heavy coatings; (h) FLUOROLON® 109 distributed by Southwest Impreglon® Sales, Inc. of Texas; (i) Impreglon 216® or Impreglon 872® distributed by Southwest Impreglon® Sales, Inc.; and (j) other epoxy based coatings, thermoplastic copolymers, or fluorocarbon resins. It will be appreciated that other materials can be used for the dielectric coating 738 and thus the foregoing materials provide examples that are not intended to limit the claims. The dielectric coating 738 can be removed from the contact site 749 to expose the contact layer 736 on the raised feature 740 using a laser ablation technique. As a result, the dielectric coating 738 can have an aperture 739 with a stepped edge to inhibit the metal in any plating solution that leaks past the seal 790 from plating over the dielectric coating 738 adjacent to the aperture 739. In this embodiment, the raised feature 740 is a deformed portion of the biasing element 735, and the contact layer 736 is a conformal layer that is plated onto the biasing element 735. The raised feature can alternatively be a separate bump of material (e.g., platinum) that is deposited on the biasing element.

The shield 770 of the contact assembly 700 shown in FIG. 7 can also include a lateral section 772, and the seal 790 can be molded or otherwise adhered to the shield 770. The shield 770 and the seal 790 can have any of the configurations and be formed of any of the materials set forth above with reference to FIGS. 3–6. In an alternative embodiment, the seal 790 can extend radially outwardly beyond the boundary line such that the seal 790 may extend under the contact system 730.

The contact assembly 700 is expected to further protect the contact members 734 without pressurizing the area around the contact system 730. The performance of the contact assembly 700 is enhanced because the contact members 734 are not only protected by the shield 770 and seal 790, but they are also protected by the dielectric coating 738. As a result, small leaks between the seal 790 and the workpiece may not pose a problem because the dielectric layer 738 still prevents the electroplating solution from plating the contact members.

From the foregoing it will be appreciated that specific embodiments of the invention have been described herein for purposes of illustration, but that various modifications may be made without deviating from the spirit and scope of the invention. For example, the contact assemblies 200 and 700 can have contact systems in accordance with any of the embodiments set forth in U.S. application Ser. No. 09/717, 927 or PCT Application No. PCT/US99/15847. Additionally, the contact assemblies described above can be used in any of the chambers disclosed in PCT Application Nos. PCT/US00/10210 and PCT/US00/10120. In still additional embodiments, the contact system 730 of the contact assembly 700 does not have a raised feature 740 at the contact site, but rather the dielectric coating 738 is removed from the top surface of the tips of the contact members 734 to define the contact sites. Accordingly, the invention is not limited except by the appended claims.

What is claimed it:

1. A contact assembly for plating a layer on a microelectronic workpiece, comprising:

a support member having an opening configured to receive a microelectronic workpiece;

a contact system carried by the support member, the contact system having a plurality of electrically conductive contact members projecting inwardly into the opening;

a shield carried by the support member to prevent electroplating solution from engaging the contact members, the shield projecting from the support member to extend under the contact members and into the opening, and the shield including a lip region in the opening inwardly of the contact members; and an elastomeric seal molded onto the lip region of the shield to adhere the seal to the shield.

2. The contact assembly of claim 1 wherein the shield is composed of polyetheretherketone and the seal is composed of a fluoroelastomer.

3. The contact assembly of claim 1 wherein the shield is composed of polyetheretherketone and the seal is composed of a perfluoroelastomer.

4. The contact assembly of claim 1 wherein the shield is composed of polyvinylidene fluoride and the seal is composed of a fluoroelastomer.

5. The contact assembly of claim 1 wherein the shield is composed of polyvinylidene fluoride and the seal is composed of a perfluoroelastomer.

6. The contact assembly of claim 1 wherein the contact assembly further comprises an adhesive between the seat and the shield.

7. The contact assembly of claim 1 wherein the lip region of the shield and the seal have a thickness of not greater than approximately 0.1 inch.

8. The contact assembly of claim 1 wherein the lip region of the shield and the seal have a thickness of not greater than approximately 0.085 inch.

9. The contact assembly of claim 1 wherein the seal has a width of not greater than approximately 0.055 inch.

10. The contact assembly of claim 1 wherein the seal has a width of not greater than approximately 0.035 inch.

11. The contact assembly of claim 1 wherein:
the support member comprises an annular ring composed of a conductive material;
the contact system comprises a ring contact having an annular base attached to the support member and a plurality of fingers projecting generally radially inwardly from the base into the opening, the contact ring being composed of a conductive material; and
the shield comprises a dielectric material attached to the support member.

12. The contact assembly of claim 1 wherein:
the support member comprises an annular ring composed of a conductive material;
the contact system comprises a ring contact having an annular section attached to the support member and a plurality of fingers swept at an angle relative to a radius of the support member; and
the shield comprises a dielectric material attached to the support member to electrically isolate the support member from an electroplating solution.

13. The contact assembly of claim 1 wherein:
the shield has a plurality of apertures through the lip region; and
the seal has an upper section on the lip region and a lower section in the apertures.

14. The contact assembly of claim 1 wherein:
the support member comprises an annular ring composed of a conductive material;
the contact system comprises a ring contact having an annular section attached to the support member and a plurality of fingers swept at an angle relative to a radius of the support member, wherein the fingers each have a contact site configured to electrically contact the workpiece and a dielectric coating around the contact site; and
the shield comprises a dielectric material attached to the support member to electrically isolate the support member from an electroplating solution.

15. A contact assembly for plating a layer on a microelectronic workpiece, comprising:
a support member having an opening configured to receive a microelectronic workpiece;
a contact system carried by the support member, the contact system having a plurality of electrically conductive contact members projecting from the support member to contact sites;
a shield carried by the support member to prevent electroplating solution from engaging the contact members, the shield being a flexible member extending under the contact members to an interior location of the opening inwardly of the contact members, and the shield having an inner edge inward of the contact sites of the contact members and a boundary line between the inner edge and the contact sites; and
an elastomeric seal adhered to the shield, the seal having a first edge at the inner edge of the shield and a second edge at the boundary line of the shield that defines an outermost perimeter of the seal.

16. The contact assembly of claim 15 wherein:
the support member comprises an annular ring composed of a conductive material;
the contact system comprises a ring contact having an annular base attached to the support member and a plurality of fingers projecting generally radially inwardly from the base into the opening, the contact ring being composed of a conductive material; and
the shield comprises a dielectric material attached to the support member.

17. The contact assembly of claim 15 wherein:
the support member comprises an annular ring composed of a conductive material;
the contact system comprises a ring contact having an annular section attached to the support member and a plurality of fingers swept at an angle relative to a radius of the support member; and
the shield comprises a dielectric material attached to the support member to electrically isolate the support member from an electroplating solution.

18. The contact assembly of claim 15 wherein:
the shield has a plurality of apertures; and
the seal has an upper section on the shield and a lower section in the apertures.

19. The contact assembly of claim 15 wherein:
the support member comprises an annular ring composed of a conductive material;
the contact system comprises a ring contact having an annular section attached to the support member and a plurality of fingers swept at an angle relative to a radius of the support member, wherein the fingers each have a contact site configured to electrically contact the workpiece and a dielectric coating around the contact site; and
the shield comprises a dielectric material attached to the support member to electrically isolate the support member from an electroplating solution.

20. The contact assembly of claim 15 wherein the shield and the seal have a thickness of not greater than approximately 0.085 inch.

21. The contact assembly of claim 15 wherein the seal has a width of not greater than approximately 0.055 inch.

22. A contact assembly for plating a layer on microelectronic workpiece, comprising:

a support member having an opening configured to receive a microelectronic workpiece;

a plurality of contact members carried by the support member, the contact members being a plurality of fingers projecting inwardly into the opening, and the fingers having contact sites;

a shield carried by the support member, the shield extending under the contact members and projecting radially inwardly into the opening of the support member to an interior location radially inwardly of the contact sites; and a seal attached to the interior location of the shield, wherein the seal is molded onto the shield.

23. The contact assembly of claim 22 wherein:

the support member comprises an annular ring composed of a conductive material;

the contact members comprise fingers projecting from an annular base attached to the support member, wherein the fingers project generally radially inwardly from the base into the opening, and the base is composed of a conductive material; and the shield comprises a dielectric material attached to the support member.

24. The contact assembly of claim 22 wherein:

the support member comprises an annular ring composed of a conductive material;

the contact members comprise fingers projecting from an annular section attached to the support member, wherein the fingers are swept at an angle relative to a radius of the support member; and the shield comprises a dielectric material attached to the support member to electrically isolate the support member from an electroplating solution.

25. The contact assembly of claim 22 wherein:

the shield has a plurality of apertures; and the seal has an upper section on the shield and a lower section in the apertures.

26. The contact assembly of claim 22 wherein the contact members each have a contact site configured to electrically contact the workpiece and a dielectric coating around the contact site.

27. A contact assembly for plating a layer on microelectronic workpiece, comprising:

a support member having an opening configured to receive a microelectronic workpiece wherein the support member is composed of a conductive material;

a plurality of contact members carried by the support member, the contact members being a plurality of fingers projecting inwardly into the opening, and the fingers having contact sites;

a shield carried by the support member, the shield extending under the contact members and projecting radially inwardly into the opening of the support member to an interior location radially inwardly of the contact sites, wherein the shield is composed of a dielectric material; and a seal attached to the interior location of the shield, wherein the seal is molded onto the shield and the seal is composed of an elastomer.

28. A contact assembly for plating a layer on microelectronic workpiece, comprising:

a support member having an opening configured to receive a microelectronic workpiece;

a plurality of contact members carried by the support member, the contact members being a plurality of fingers projecting inwardly into the opening, and the fingers having contact sites;

a shield carried by the support member, the shield extending under the contact members and projecting radially inwardly into the opening of the support member to an interior location radially inwardly of the contact sites; and a seal attached to the interior location of the shield, the seal being molded onto the shield, and the seal having a width of approximately 0.02–0.04 inch.

29. A contact assembly for plating a layer on microelectronic workpiece, comprising:

a support member having an opening configured to receive a microelectronic workpiece;

a plurality of contact members carried by the support member, the contact members being a plurality of fingers projecting inwardly into the opening, and the fingers having contact sites;

a shield carried by the support member, the shield extending under the contact members and projecting radially inwardly into the opening of the support member to an interior location radially inwardly of the contact sites; and a seal attached to the interior location of the shield, the seal being molded onto the shield, the seal having a width of approximately 0.02–0.04 inch, and the seal and the interior location of the shield having a thickness of approximately 0.04–0.10 inch.

30. A contact assembly for use in an electrochemical deposition system to apply an electrical potential to a microelectronic workpiece, the contact assembly comprising:

a support member having an opening configured to receive the workpiece;

a contact system carried by the support member, the contact system having a plurality of contact members projecting inwardly into the opening relative to the support member, wherein the contact members each have a contact site configured to electrically contact the workpiece and a dielectric coating around the contact site;

a shield carried by the support member, the shield projecting from the support member to extend under, the contact members and into the opening, and the shield including a lip region inwardly of the contact members; and an elastomeric seal on the lip region of the shield.

31. The contact assembly of claim 30 wherein the contact members comprise cantilevered spring elements projecting upwardly into the opening.

32. The contact assembly of claim 30 wherein the contact members comprise cantilevered spring elements projecting upwardly into the opening, and the cantilevered spring elements have a raised feature.

33. The contact assembly of claim 30 wherein the contact members comprise cantilevered spring elements projecting upwardly into the opening, and the cantilevered spring elements have a raised feature comprising a deformed section of the spring elements.

34. The contact assembly of claim 30 wherein:

the support member comprises a conductive support ring and a dielectric coating on at least a portion of the support ring;

the contact system further comprises a conductive mounting section attached directly to the support ring; and the contact members are fingers integral with the mounting section.

35. The contact assembly of claim 34 wherein the mounting section comprises an arcuate element and the fingers project inwardly from the arcuate element along a radius of the support ring.

36. The contact assembly of claim 34 wherein the mounting section comprises an arcuate element and the fingers project inwardly from the arcuate element along a radius of the support ring, and the fingers have a raised contact feature.

37. The contact assembly of claim 34 wherein the mounting section comprises an arcuate element and the fingers project inwardly from the arcuate element at an angle relative to a radius of the support ring.

38. The contact assembly of claim 34 wherein the mounting section comprises an arcuate element and the fingers project inwardly from the arcuate element at an angle relative to a radius of the support ring, and the fingers have a raised contact feature.

39. The contact assembly of claim 30 wherein:
the support member comprises an annular ring composed of a conductive material;
the contact system comprises a ring contact having an annular base attached to the support member and a plurality of fingers projecting generally radially inwardly from the base into the opening, the contact ring being composed of a conductive material; and
the shield comprises a dielectric material attached to the support member.

40. The contact assembly of claim 30 wherein:
the support member comprises an annular ring composed of a conductive material;
the contact system comprises a ring contact having an annular section attached to the support member and a plurality of fingers swept at an angle relative to a radius of the support member; and
the shield comprises a dielectric material attached to the support member to electrically isolate the support member from an electroplating solution.

41. The contact assembly of claim 30 wherein:
the shield has a plurality of apertures through the lip region; and
the seal has an upper section on the lip region and a lower section in the apertures.

42. The contact assembly of claim 34 wherein:
the support member comprises an annular ring composed of a conductive material;
the contact system comprises a ring contact having an annular section attached to the support member and a plurality of fingers swept at an angle relative to a radius of the support member, wherein the fingers each have a contact site configured to electrically contact the workpiece and a dielectric coating around the contact site; and
the shield comprises a dielectric material attached to the support member to electrically isolate the support member from an electroplating solution.

43. A reactor system for electroplating microelectronic workpieces, comprising:
a bowl configured to hold a plating solution;
an anode in the bowl at a location to contact the plating solution;
a head assembly moveable relative to the bowl between a first position to load/unload a workpiece and a second position to place at least a portion of the workpiece in the plating solution; and
a contact assembly comprising a support member having an opening configured to receive a microelectronic workpiece; a contact system carried by the support member, the contact system having a plurality of electrically conductive contact members projecting inwardly into the opening; a shield carried by the support member to prevent electroplating solution from engaging the contact members the shield projecting from the support member to extend under the contact members and into opening, and the shield including a lip region in the opening inwardly of the contact members: and an elastomeric seal molded onto the lip region to adhere the seal to the shield.

44. The reactor system of claim 43 wherein the shield is composed of polyetheretherketone and the seal is composed of a fluoroelastomer.

45. The reactor system of claim 43 wherein the shield is composed of polyetheretherketone and the seal is composed of a perfluoroelastomer.

46. The reactor system of claim 43 wherein the shield is composed of polyvinylidene fluoride and the seal is composed of a fluoroelastomer.

47. The reactor system of claim 43 wherein the shield is composed of polyvinylidene fluoride and the seal is composed of a perfluoroelastomer.

48. The reactor system of claim 43 wherein the contact assembly further comprises an adhesive between the seal and the shield.

49. The reactor system of claim 43 wherein the lip region of the shield and the seal have a thickness of not greater than approximately 0.1 inch.

50. The reactor system of claim 43 wherein the lip region of the shield and the seal have a thickness of not greater than approximately 0.085 inch.

51. The reactor system of claim 43 wherein the seal has a width of not greater than approximately 0.055 inch.

52. The reactor system of claim 43 wherein the seal has a width of not greater than approximately 0.035 inch.

53. The reactor system of claim 43 wherein:
the support member comprises an annular ring composed of a conductive material;
the contact system comprises a ring contact having an annular base attached to the support member and a plurality of fingers projecting generally radially inwardly from the base into the opening, the contact ring being composed of a conductive material; and
the shield comprises a dielectric material attached to the support member.

54. The reactor system of claim 43 wherein:
the support member comprises an annular ring composed of a conductive material;
the contact system comprises a ring contact having an annular section attached to the support member and a plurality of fingers swept at an angle relative to a radius of the support member; and
the shield comprises a dielectric material attached to the support member to electrically isolate the support member from an electroplating solution.

55. The reactor system of claim 43 wherein:
the shield has a plurality of apertures through the lip region; and
the seal has an upper section on the lip region and a lower section in the apertures.

56. The reactor system of claim 43 wherein:

the support member comprises an annular ring composed of a conductive material;

the contact system comprises a ring contact having an annular section attached to the support member and a plurality of fingers swept at an angle relative to a radius of the support member, wherein the fingers each have a contact site configured to electrically contact the workpiece and a dielectric coating around the contact site; and the shield comprises a dielectric material attached to the support member to electrically isolate the support member from an electroplating solution.

57. A reactor system for electroplating microelectronic workpieces, comprising:

a bowl configured to hold a plating solution;

an anode in the bowl at a location to contact the plating solution;

a head assembly moveable relative to the bowl between a first position to toad/unload a workpiece and a second position to place at least a portion of the workpiece in the plating solution; and a contact assembly comprising a support member having an opening configured to receive a microelectronic workpiece; a contact system carried by the support member, the contact system having a plurality of electrically conductive contact members projecting inwardly into the opening; a shield carried by the support member to prevent electroplating solution from engaging the contact members, the shield being a flexible member extending under the contact members to an interior location of the opening inwardly of the contact members, and the shield having a lip region in the opening inwardly of the contact members; and an elastomeric seal adhered to the lip region of the shield, the seal having a first edge at an inner edge of the lip region and a second edge at a boundary line of the shield between the inner edge and the contact members, wherein the second edge of the seal defines an outer perimeter of the seal.

58. The reactor system of claim 57 wherein:

the support member comprises an annular ring composed of a conductive material;

the contact system comprises a ring contact having an annular base attached to the support member and a plurality of fingers projecting generally radially inwardly from the base into the opening, the contact ring being composed of a conductive material; and the shield comprises a dielectric material attached to the support member.

59. The reactor system of claim 57 wherein:

the support member comprises an annular ring composed of a conductive material, the contact system comprises a ring contact having an annular section attached to the support member and a plurality of fingers swept at an angle relative to a radius of the support member; and the shield comprises a dielectric material attached to the support member to electrically isolate the support member from an electroplating solution.

60. The reactor system of claim 57 wherein:

the shield has a plurality of apertures through the lip region; and the seal has an upper section on the lip region and a lower section in the apertures.

61. The reactor system of claim 57 wherein the contact members each have a contact site configured to electrically contact the workpiece and a dielectric coating around the contact site.

62. The reactor system of claim 57 wherein the lip region of the shield and the seal have a thickness of not greater than approximately 0.085 inch.

63. The reactor system of claim 57 wherein the seal has a width of not greater than approximately 0.055 inch.

64. A reactor system for electroplating microelectronic workpieces, comprising:

a bowl configured to hold a plating solution, an anode in the bowl at a location to contact the plating solution;

a head assembly moveable relative to the bowl between a first position to load/unload a workpiece and a second position to place at least a portion of the workpiece in the plating solution; and a contact assembly comprising a support member having an opening configured to receive a microelectronic workpiece; a plurality of contact members carried by the support member, the contact members being a plurality of fingers projecting inwardly into the opening, and the fingers having contact sites; a shield carried by the support member, the shield extending under the contact members and projecting radially inwardly into the opening of the support member to an interior location radially inwardly of the contact sites; and a seal attached to the interior location of the shield, wherein the seal is molded onto the shield.

65. The reactor system of claim 64 wherein:

the support member comprises an annular ring composed of a conductive material;

the contact members are integral with an annular base attached to the support member and project generally radially inwardly from the base into the opening, the annular base being composed of a conductive material; and the shield comprises a dielectric material attached to the support member.

66. The reactor system of claim 64 wherein:

the support member comprises an annular ring composed of a conductive material;

the contact members are integral with an annular section attached to the support member and project inwardly at an angle relative to a radius of the support member; and the shield comprises a dielectric material attached to the support member to electrically isolate the support member from an electroplating solution.

67. The reactor system of claim 64 wherein:

the shield has a plurality of apertures; and the seal has an upper section on the shield and a lower section in the apertures.

68. A reactor system for electroplating microelectronic workpieces, comprising:

a bowl configured to hold a plating solution;

an anode in the bowl at a location to contact the plating solution;

a head assembly moveable relative to the bowl between a first position to load/unload a workpiece and a second position to place at least a portion of the workpiece in the plating solution; and a contact assembly comprising a support member having an opening configured to receive a microelectronic workpiece; a plurality of contact members carried by the support member, the contact members being a plurality of fingers projecting inwardly into the opening, and the fingers having contact sites; a shield carried by the support member, the shield extending under the contact members and projecting radially inwardly into the opening of the support member to an interior location radially inwardly of the contact sites, wherein the shield is composed of a plastic; and a seal attached to the interior location of the shield, wherein the seal is molded onto the shield and the seal is composed of an elastomer.

69. A reactor system for electroplating microelectronic workpieces, comprising:

a bowl configured to hold a plating solution;

an anode in the bowl at a location to contact the plating solution;

a head assembly moveable relative to the bowl between a first position to load/unload a workpiece and a second position to place at least a portion of the workpiece in the plating solution; and a contact assembly comprising a support member having an opening configured to receive a microelectronic workpiece; a plurality of contact members carried by the support member, the contact members being a plurality of fingers projecting inwardly into the opening, and the fingers having contact sites; a shield carried by the support member, the shield extending under the contact members and projecting radially inwardly into the opening of the support member to an interior location radially inwardly of the contact sites; and a seal attached to the interior location of the shield, the seal being molded onto the shield, and the seal having a width of approximately 0.02–0.04 inch.

70. A reactor system for electroplating microelectronic workpieces, comprising:

a bowl configured to hold a plating solution;

an anode in the bowl at a location to contact the plating solution;

a head assembly moveable relative to the bowl between a first position to load/unload a workpiece and a second position to place at least a portion of the workpiece in the plating solution; and a contact assembly comprising a support member having an opening configured to receive a microelectronic workpiece; a plurality of contact members carried by the support member, the contact members being a plurality of fingers projecting inwardly into the opening, and the fingers having contact sites; a shield carried by the support member, the shield extending under the contact members and projecting radially inwardly into the opening of the support member to an interior location radially inwardly of the contact sites; and a seal attached to the interior location of the shield, the seal being molded onto the shield, the seal having a width of approximately 0.02–0.04 inch, and the seal and the interior location of the shield having a thickness of approximately 0.04–0.10 inch.

* * * * *

UNITED STATES PATENT AND TRADEMARK OFFICE
CERTIFICATE OF CORRECTION

PATENT NO. : 6,773,560 B2
DATED : August 10, 2004
INVENTOR(S) : John M. Pedersen et al.

It is certified that error appears in the above-identified patent and that said Letters Patent is hereby corrected as shown below:

Column 13,
Line 16, "seat" should be -- seal --;

Column 19,
Line 20, "toad" should be -- load --;

Signed and Sealed this

Fifteenth Day of February, 2005

JON W. DUDAS
*Director of the United States Patent and Trademark Office*